(12) United States Patent
Sasaki

(10) Patent No.: US 8,008,485 B2
(45) Date of Patent: Aug. 30, 2011

(54) PROCESS FOR PRODUCING 2,3-DIHYDROPYRIDAZINE COMPOUND

(75) Inventor: Kazuaki Sasaki, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 498 days.

(21) Appl. No.: 12/064,629

(22) PCT Filed: Aug. 22, 2006

(86) PCT No.: PCT/JP2006/316797
§ 371 (c)(1),
(2), (4) Date: Feb. 23, 2008

(87) PCT Pub. No.: WO2007/026624
PCT Pub. Date: Mar. 8, 2007

(65) Prior Publication Data
US 2009/0105475 A1    Apr. 23, 2009

(30) Foreign Application Priority Data
Aug. 30, 2005 (JP) ................. 2005-248844

(51) Int. Cl.
*C07D 237/20* (2006.01)
*A61P 33/00* (2006.01)

(52) U.S. Cl. ................................ 544/224

(58) Field of Classification Search ............ 544/224
See application file for complete search history.

(56) References Cited

FOREIGN PATENT DOCUMENTS
JP    1-316379 A    12/1989

OTHER PUBLICATIONS
English translation of Degot, et al., SU 642310, published 19790115.*
English translation of Nakahama, et al., JP 01316379, published 19891221.*

\* cited by examiner

*Primary Examiner* — James O Wilson
*Assistant Examiner* — Cecilia M Jaisle
(74) *Attorney, Agent, or Firm* — Panitch Schwarze Belisario & Nadel LLP

(57) ABSTRACT

A process for producing a 2,3-dihydropyridazine compound represented by the formula (2):

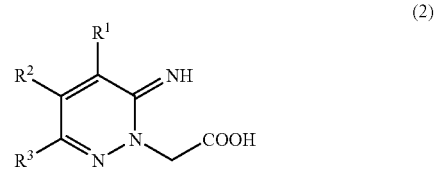

(2)

wherein $R^1$, $R^2$ and $R^3$ are the same or different and each represents a hydrogen atom, a halogen atom, an alkyl group which may be substituted with a halogen atom or atoms, an alkenyl group which may be substituted with a halogen atom or atoms, an alkoxy group which may be substituted with a halogen atom or atoms, an alkylthio group, an alkylsulfenyl group, an alkylsulfonyl group or a dialkylamino group;
which comprises reacting a salt consisting of bromoacetic acid and an amine compound with a pyridazine compound represented by the formula (1):

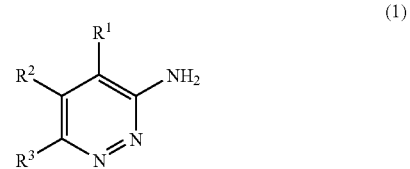

(1)

wherein $R^1$, $R^2$ and $R^3$ are the same meanings as defined above.

7 Claims, No Drawings

PROCESS FOR PRODUCING 2,3-DIHYDROPYRIDAZINE COMPOUND

CROSS-REFERENCE TO RELATED APPLICATION

This application is a section 371 of International Application No. PCT/JP2006/316797, filed Aug. 22, 2006, which was published in the Japanese language on Mar. 8, 2007 under International Publication No. WO 2007/026624 A1 and the disclosure of which is incorporated herein by reference.

TECHNICAL FIELD

The present invention relates to a process for producing a 2,3-dihydropyridazine compound.

BACKGROUND ART

A 2,3-dihydropyridazine compound represented by the formula (2):

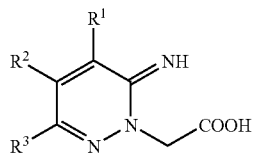
(2)

wherein $R^1$, $R^2$ and $R^3$ are the same or different and each represents a hydrogen atom, a halogen atom, an alkyl group which may be substituted with a halogen atom or atoms, an alkenyl group which may be substituted with a halogen atom or atoms, an alkoxy group which may be substituted with a halogen atom or atoms, an alkylthio group, an alkylsulfenyl group, an alkylsulfonyl group or a dialkylamino group, is useful as an intermediate of pharmaceuticals and pesticides. For example, 3-imino-6-chloro-2,3-dihydropyridazine-2-acetic acid has been known as an intermediate of sulfonylurea herbicides (e.g. U.S. Pat. No. 4,017,212 and U.S. Pat. No. 4,994,571), and as processes for producing it, a process comprising reacting a salt consisting of chloroacetic acid and triethylamine with 3-amino-6-chloropyridazine (e.g. JP patent No. 2,863,857).

DISCLOSURE OF THE INVENTION

The present invention provides a process for producing a 2,3-dihydropyridazine compound represented by the formula (2):

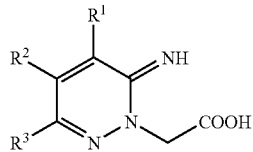
(2)

wherein $R^1$, $R^2$ and $R^3$ are the same or different and each represents a hydrogen atom, a halogen atom, an alkyl group which may be substituted with a halogen atom or atoms, an alkenyl group which may be substituted with a halogen atom or atoms, an alkoxy group which may be substituted with a halogen atom or atoms, an alkylthio group, an alkylsulfenyl group, an alkylsulfonyl group or a dialkylamino group;
which comprises reacting a salt consisting of bromoacetic acid and an amine compound with a pyridazine compound represented by the formula (1):

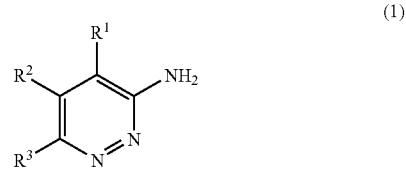
(1)

wherein $R^1$, $R^2$ and $R^3$ are the same meanings as defined above.

BEST MODE FOR CARRYING OUT THE PRESENT INVENTION

In the formula of the pyridazine compound represented by the formula (1):

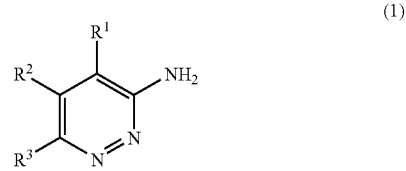
(1)

(hereinafter, simply referred to as the pyridazine compound (1)), $R^1$, $R^2$ and $R^3$ are the same or different and each represents a hydrogen atom, a halogen atom, an alkyl group which may be substituted with a halogen atom or atoms, an alkenyl group which may be substituted with a halogen atom or atoms, an alkoxy group which may be substituted with a halogen atom or atoms, an alkylthio group, an alkylsulfenyl group, an alkylsulfonyl group or a dialkylamino group.

Examples of the halogen atom include a fluorine atom, a chlorine atom and a bromine atom.

Examples of the alkyl group which may be substituted with a halogen atom or atoms include a C1-C6 linear, branched chain or cyclic unsubstituted alkyl group such a methyl, ethyl, n-propyl, isopropyl, n-butyl, isobutyl, sec-butyl, tert-butyl, n-pentyl, n-hexyl, cyclopentyl and cyclohexyl group; and those wherein at least one hydrogen atom of the above-mentioned unsubstituted alkyl groups is substituted with the above-mentioned halogen atom such as a fluoromethyl, chloromethyl, bromomethyl, trifluoromethyl, 1-chloroethyl, 1-bromoethyl, 1,1,1-trifluoroethyl, 1-chloropropyl, 1-bromopropyl and 1,1,1-trifluoropropyl group.

Examples of the alkenyl group which may be substituted with a halogen atom or atoms include a C2-C6 linear, branched chain or cyclic unsubstituted alkenyl group such as a vinyl, 1-propenyl, 2-propenyl, 2-methyl-1-propenyl, 1,2-propadienyl, 1-butenyl, 2-butenyl, 1,3-butadienyl, 1-pentenyl, 1-hexenyl and 1-cyclohexenyl group; and those wherein at least one hydrogen atom of the above-mentioned unsubstituted alkenyl groups is substituted with the above-mentioned halogen atom such as a 2-chloro-1-propenyl, 2,2-dichlorovinyl, 2-chloro-2-fluoroethenyl and 3-bromo-1-methyl-1-propenyl group.

Examples of the alkoxy group which may be substituted with a halogen atom or atoms include a C1-C6 linear or branched chain unsubstituted alkoxy group such a methoxy, ethoxy, n-propoxy, isopropoxy, n-butoxy, sec-butoxy, tert-butoxy, n-pentyloxy, n-hexyloxy, cyclopropyloxy, cyclopentyloxy and cyclohexyloxy group; and those wherein at least one hydrogen atom of the above-mentioned unsubstituted alkoxy groups is substituted with the above-mentioned halogen atom such as a fluoromethoxy, chloromethoxy, bromomethoxy, trifluoromethoxy, 1-chloroethoxy, 1-bromoethoxy, 1,1,1-trifluoroethoxy, 1-chloropropoxy, 1-bromopropoxy and 1,1,1-trifluoropropoxy group.

Examples of the alkylthio group include those wherein the oxygen atom of the above-mentioned unsubstituted alkoxy group is substituted with a sulfur atom such as a methylthio, ethylthio, n-propylthio, isopropylthio, n-butylthio, sec-butylthio, tert-butylthio, n-pentylthio, n-hexylthio, cyclopropylthio, cyclopentylthio and cyclohexylthio group.

Examples of the alkylsulfenyl group include those composed of the above-mentioned unsubstituted alkyl group and a sulfenyl group such as a methylsulfenyl, ethylsulfenyl, n-propylsulfenyl, isopropylsulfenyl, n-butylsulfenyl, sec-butylsulfenyl, tert-butylsulfenyl, n-pentylsulfenyl, n-hexylsulfenyl, cyclopropylsulfenyl, cyclopentylsulfenyl and cyclohexylsulfenyl group.

Examples of the alkylsulfonyl group include those composed of the above-mentioned unsubstituted alkyl group and a sulfonyl group such as a methylsulfonyl, ethylsulfonyl, n-propylsulfonyl, isopropylsulfonyl, n-butylsulfonyl, sec-butylsulfonyl, tert-butylsulfonyl, n-pentylsulfonyl, n-hexylsulfonyl, cyclopropylsulfonyl, cyclopentylsulfonyl and cyclohexylsulfonyl group.

The dialkylamino group is an amino group substituted with two above-mentioned unsubstituted alkyl groups and two unsubstituted alkyl groups may be the same or different. Two unsubstituted alkyl groups may be bonded to form a cyclic amino group together with the nitrogen atom to which they are bonded. Examples of the dialkylamino group include a dimethylamino, diethylamino, di-n-propylamino, diisopropylamino, di-n-butylamino, di-n-hexylamino, dicyclopropylamino, dicyclopentylamino, dicyclohexylamino, methylethylamino, ethylisopropylamino, aziridino, pyrrolidino and piperidino group.

Examples of the pyridazine compound (1) include 3-aminopyridazine, 3-amino-6-chloropyridazine, 3-amino-6-methylpyridazine, 3-amino-6-dimethylaminopyridazine, 3-amino-6-methoxypyridazine, 3-amino-6-ethoxypyridazine, 3-amino-6-methylthiopyridazine, 3-amino-6-methanesulfonylpyridazine, 3-amino-6-trifluoromethylpyridazine, 3-amino-4-methylpyridazine, 3-amino-4-methyl-6-dimethylaminopyridazine and 3-amino-4-methyl-6-methylthiopyridazine.

As the pyridazine compound (1), a commercially available one may be used and one produced according to the method described, for example, in JP patent No. 3,012,993 may be used.

The salt consisting of bromoacetic acid and the amine compound is usually prepared by reacting bromoacetic acid with the amine compound in the presence of a solvent.

As the amine compound, a tertiary amine such as trimethylamine, triethylamine, tri(n-propyl)amine, diisopropylmethylamine, diisopropylethylamine, tri(n-butyl)amine, dicyclohexylmethylamine and dimethylcyclohexylamine is preferably used.

As bromoacetic acid and the amine compound, the commercially available ones can usually be used. The amount of the amine compound to be used is usually 0.9 to 1.1 moles relative to 1 mole of bromoacetic acid.

The above-mentioned solvent is not particularly limited as far as it is one in which the salt consisting of bromoacetic acid and the amine compound can be soluble. Examples thereof include water; an alcohol solvent such as methanol, ethanol and isopropanol; and an ether solvent such as diethyl ether, methyl isobutyl ether, methyl tert-butyl ether and tetrahydrofuran. These solvents may be used alone or in a form of a mixture. The amount of the solvent to be used is not particularly limited.

The preparing temperature of the salt consisting of bromoacetic acid and the amine compound is usually −50 to 30° C. and preferably −10 to 20° C.

The mixing order of bromoacetic acid and the amine compound is not particularly limited and preferred examples thereof include a method comprising mixing bromoacetic acid and the solvent and then adding the amine compound to the mixture obtained.

The reaction mixture containing the salt consisting of bromoacetic acid and the amine compound obtained may be used as it is in the reaction with the pyridazine compound (1), and the salt consisting of bromoacetic acid and the amine compound may be isolated from the reaction mixture by concentration or the like, and then used it in the reaction with the pyridazine compound (1). A part of the solvent may be distilled away from the reaction mixture to prepare slurry of the salt consisting of bromoacetic acid and the amine compound and then slurry may be used in the reaction with the pyridazine compound (1). The reaction mixture containing the salt consisting of bromoacetic acid and the amine compound obtained is preferably used as it is.

The pyridazine compound (1) may be previously mixed with the solvent. Examples of the solvent include the same solvents as those exemplified as the solvent used in preparation of the salt consisting of bromoacetic acid and the amine compound, and the same solvent as used in preparation of the salt consisting of bromoacetic acid and the amine compound is preferably used. The amount thereof to be used is not particularly limited.

The amount of the salt consisting of bromoacetic acid and the amine compound is usually 1 mole or more based on bromoacetic acid relative to 1 mole of the pyridazine compound (1), and preferably 1.1 to 2 moles.

The temperature of the reaction of the salt consisting of bromoacetic acid and the amine compound and the pyridazine compound (1) is usually between 20° C. and the boiling point of the solvent used, and preferably 40 to 60° C.

The reaction of the salt consisting of bromoacetic acid and the amine compound and the pyridazine compound (1) is usually conducted by mixing the both. The mixing order is not particularly limited, and the salt consisting of bromoacetic acid and the amine compound is preferably added to the pyridazine compound (1) or a mixture of the pyridazine compound (1) and the solvent. In the viewpoint of stability of the salt consisting of bromoacetic acid and the amine compound, the salt consisting of bromoacetic acid and the amine compound is preferably kept at −50 to 30° C. The time from preparing the salt consisting of bromoacetic acid and the amine compound to mixing the all amount thereof with the pyridazine compound (1) is usually within 50 hours and preferably within 24 hours.

A 2,3-dihydropyridazine compound represented by the formula (2):

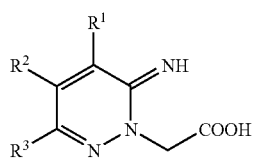

(hereinafter, simply referred to as the 2,3-dihydropyridazine compound (2)) is obtained by mixing the salt consisting of bromoacetic acid and the amine compound with the pyridazine compound (1) and then keeping the resultant mixture at the predetermined temperature to effect reaction. The reaction time is usually 1 to 24 hours. The progress of the reaction can be confirmed by a conventional analytical means such as gas chromatography, high performance liquid chromatography and thin layer chromatography.

After completion of the reaction, for example, the 2,3-dihydropyridazine compound (2) can be isolated by cooling the reaction mixture and filtrating the solids precipitated. The 2,3-dihydropyridazine compound (2) isolated may be further purified, for example, by a conventional purification means such as recrystallization and column chromatography.

Examples of the 2,3-dihydropyridazine compound (2) include 3-imino-2,3-dihydropyridazine-2-acetic acid, 3-imino-6-chloro-2,3-dihydropyridazine-2-acetic acid, 3-imino-6-methyl-2,3-dihydropyridazine-2-acetic acid, 3-imino-6-(dimethylamino)-2,3-dihydropyridazine-2-acetic acid, 3-imino-6-methoxy-2,3-dihydropyridazine-2-acetic acid, 3-imino-6-ethoxy-2,3-dihydropyridazine-2-acetic acid, 3-imino-6-methylthio-2,3-dihydropyridazine-2-acetic acid, 3-imino-6-methanesulfonyl-2,3-dihydropyridazine-2-acetic acid, 3-imino-6-trifluoromethyl-2,3-dihydropyridazine-2-acetic acid, 3-imino-4-methyl-2,3-dihydropyridazine-2-acetic acid, 3-imino-4-methyl-6-dimethylamino-2,3-dihydropyridazine-2-acetic acid, and 3-imino-4-methyl-6-methylthio-2,3-dihydropyridazine-2-acetic acid.

EXAMPLES

The present invention will be further illustrated by Examples in detail below, but the present invention is not limited by these Examples. The analysis was conducted using the high performance liquid chromatography internal standard method.

Example 1

164.6 g of bromoacetic acid and 200 g of 10% by weight hydrous methanol were mixed and the inner temperature of the solution obtained was adjusted to 5° C. While keeping the inner temperature thereof at 5 to 7° C., 153.1 g of diisopropylethylamine was added to the solution over about 3 hours to obtain a solution containing the salt consisting of bromoacetic acid and diisopropylethylamine. The solution obtained was kept at the inner temperature of 5 to 7° C. for 30 minutes, and then the solution was added dropwise over 30 minutes to the mixture of 100 g of 3-amino-6-chloropyridazine (content: 99.2% by weight) and 200 g of 10% by weight hydrous methanol which was adjusted to the inner temperature of 50° C. The solution containing the salt consisting of bromoacetic acid and diisopropylethylamine was kept at the inner temperature of 5 to 7° C. until completion of the addition.

After completion of the addition, the mixture obtained was kept at the inner temperature of 50° C. for 12 hours. After completion of the reaction, the reaction mixture was cooled to the inner temperature of 5° C. over about 3 hours. The solids precipitated were separated from the reaction mixture by filtration. The solids separated were washed twice with 240 g of 10% by weight hydrous methanol water and dried under reduced pressure to obtain 130.0 g of 3-imino-6-chloro-2,3-dihydropyridazine-2-acetic acid (content: 98.3% by weight). Yield: 89%.

Example 2

164.6 g of bromoacetic acid and 200 g of 10% by weight hydrous methanol were mixed and the inner temperature of the solution obtained was adjusted to 5° C. While keeping the inner temperature thereof at 5 to 7° C., 153.1 g of diisopropylethylamine was added to the solution over about 3 hours to obtain a solution containing the salt consisting of bromoacetic acid and diisopropylethylamine. The solution obtained was kept at the inner temperature of 5 to 7° C. for 30 minutes, and then the solution was added dropwise over 3 hours to the mixture of 100 g of 3-amino-6-chloropyridazine (content: 99.2% by weight) and 200 g of 10% by weight hydrous methanol which was adjusted to the inner temperature of 50° C. The solution containing the salt consisting of bromoacetic acid and diisopropylethylamine was kept at the inner temperature of 5 to 7° C. until completion of the addition.

After completion of the addition, the mixture obtained was kept at the inner temperature of 50° C. for 13 hours. After completion of the reaction, the reaction mixture was cooled to the inner temperature of 5° C. over about 3 hours. The solids precipitated were separated from the reaction mixture by filtration. The solids separated were washed twice with 240 g of 10% by weight hydrous methanol and dried under reduced pressure to obtain 126.9 g of 3-imino-6-chloro-2,3-dihydropyridazine-2-acetic acid (content: 98.3% by weight). Yield: 87%.

Examples 3

According to the same manner as that described in Example 1, 129.6 g of 3-imino-6-chloro-2,3-dihydropyridazine-2-acetic acid (content: 97.5% by weight) was obtained except that 120.3 g of triethylamine was used in place of 153.1 g of diisopropylethylamine. Yield: 88%.

Example 4

85.8 g of bromoacetic acid and 150 g of methanol were mixed and the inner temperature of the solution obtained was adjusted to 5° C. While keeping the inner temperature thereof at 5 to 7° C., 62.5 g of triethylamine was added to the solution over about 3 hours to obtain a solution containing the salt consisting of bromoacetic acid and triethylamine. The solution obtained was kept at the inner temperature of 25° C. for 1 hour, and then the solution was added dropwise over 1.5 hours to the mixture of 50 g of 3-amino-6-chloropyridazine (content: 99.2% by weight) and 50 g of methanol which was adjusted to the inner temperature of 45° C. The solution containing the salt consisting of bromoacetic acid and triethylamine was kept at the inner temperature of 25° C. until completion of the addition.

After completion of the addition, the mixture obtained was kept at the inner temperature of 45° C. for 22 hours. After completion of the reaction, 50 g of diluted water was added to the reaction mixture, and the resultant mixture was cooled to the inner temperature of 5° C. over about 3 hours. The solids precipitated were separated from the reaction mixture by filtration. The solids separated were washed twice with 120 g of methanol and dried under reduced pressure to obtain 60.6 g of 3-imino-6-chloro-2,3-dihydropyridazine-2-acetic acid (content: 93.7% by weight). Yield: 79%.

Example 5

85.8 g of bromoacetic acid and 150 g of methanol were mixed and the inner temperature of the solution obtained was adjusted to 5° C. While keeping the inner temperature thereof at 5 to 7° C., 62.5 g of triethylamine was added to the solution over about 3 hours to obtain a solution containing the salt consisting of bromoacetic acid and triethylamine. The solution obtained was kept at the inner temperature of 25° C. for 20 hour, and then the solution was added dropwise over 1.5 hours to the mixture of 50 g of 3-amino-6-chloropyridazine (content: 99.2% by weight) and 50 g of methanol which was adjusted to the inner temperature of 45° C. The solution containing the salt consisting of bromoacetic acid and triethylamine was kept at the inner temperature of 25° C. until completion of the addition.

After completion of the addition, the mixture obtained was kept at the inner temperature of 45° C. for 22 hours. After completion of the reaction, 50 g of diluted water was added to the reaction mixture, and the resultant mixture was cooled to the inner temperature of 5° C. over about 3 hours. The solids precipitated were separated from the reaction mixture by filtration. The solids separated were washed twice with 120 g of methanol and dried under reduced pressure to obtain 48.5 g of 3-imino-6-chloro-2,3-dihydropyridazine-2-acetic acid (content: 89.6% by weight). Yield: 61%.

Example 6

85.8 g of bromoacetic acid and 150 g of 10% by weight hydrous methanol were mixed and the inner temperature of the solution obtained was adjusted to 5° C. While keeping the inner temperature thereof at 5 to 7° C., 62.5 g of triethylamine was added to the solution over about 3 hours to obtain a solution containing the salt consisting of bromoacetic acid and triethylamine. The solution obtained was kept at the inner temperature of 7° C. for 18 hour, and then the solution was added dropwise over 1.5 hours to the mixture of 50 g of 3-amino-6-chloropyridazine (content: 99.2% by weight) and 50 g of 10% by weight hydrous methanol which was adjusted to the inner temperature of 45° C. The solution containing the salt consisting of bromoacetic acid and triethylamine was kept at the inner temperature of 7° C. until completion of the addition.

After completion of the addition, the mixture obtained was kept at the inner temperature of 45° C. for 18 hours. After completion of the reaction, 50 g of diluted water was added to the reaction mixture, and the resultant mixture was cooled to the inner temperature of 5° C. over about 3 hours. The solids precipitated were separated from the reaction mixture by filtration. The solids separated were washed twice with 120 g of 10% by weight hydrous methanol and dried under reduced pressure to obtain 71.9 g of 3-imino-6-chloro-2,3-dihydropyridazine-2-acetic acid (content: 78.3% by weight). Yield: 78%.

INDUSTRIAL APPLICABILITY

According to the present invention, 3-imino-2,3-dihydropyridazine-2-acetic acid compound can be produced in good yield.

The invention claimed is:

1. A process for producing a 2,3-dihydropyridazine compound represented by the formula (2):

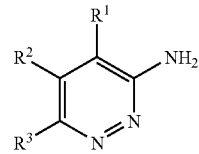

(2)

wherein $R^1$, $R^2$ and $R^3$ are the same or different and each represents a hydrogen atom, a halogen atom, an alkyl group which may be substituted with a halogen atom or atoms, an alkenyl group which may be substituted with a halogen atom or atoms, an alkoxy group which may be substituted with a halogen atom or atoms, an alkylthio group, an alkylsulfenyl group, an alkylsulfonyl group or a dialkylamino group;

which comprises reacting a salt consisting of bromoacetic acid and a tertiary amine compound with a pyridazine compound represented by the formula (1):

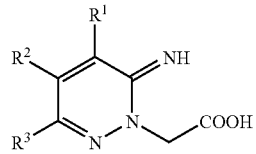

(1)

wherein $R^1$, $R^2$ and $R^3$ are the same meanings as defined above.

2. The process for producing a 2,3-dihydropyridazine compound according to claim 1, wherein the salt consisting of bromoacetic acid and a tertiary amine compound is prepared by reacting bromoacetic acid with a tertiary amine compound at −50 to 30° C. in the presence of a solvent.

3. The process for producing a 2,3-dihydropyridazine compound according to claim 2, wherein the amount of the tertiary amine compound to be used is 0.9 to 1.1 moles relative to 1 mole of bromoacetic acid.

4. The process for producing a 2,3-dihydropyridazine compound according to claim 1, wherein the salt consisting of bromoacetic acid and a tertiary amine compound is added to the pyridazine compound represented by the formula (1).

5. The process for producing a 2,3-dihydropyridazine compound according to claim 1, wherein the preparation temperature of the salt consisting of bromoacetic acid and a tertiary amine compound is −50 to 30° C.

6. The process for producing a 2,3-dihydropyridazine compound according to claim 2, wherein the time from preparing the salt consisting of bromoacetic acid and the tertiary amine compound to mixing the salt with the pyridazine compound represented by the formula (1) is within 24 hours.

7. The process for producing a 2,3-dihydropyridazine compound according to claim 1, wherein $R^1$ and $R^2$ are hydrogen atoms and $R^3$ is a chlorine atom.

* * * * *